United States Patent [19]

Liberti et al.

[11] Patent Number: 5,200,084
[45] Date of Patent: Apr. 6, 1993

[54] APPARATUS AND METHODS FOR MAGNETIC SEPARATION

[75] Inventors: Paul A. Liberti, Churchville; Brian P. Feeley, Easton; Dhanesh I. Gohel, Philadelphia, all of Pa.

[73] Assignee: Immunicon Corporation, Huntingdon Valley, Pa.

[21] Appl. No.: 588,662

[22] Filed: Sep. 26, 1990

[51] Int. Cl.$^5$ .................................................. B01D 1/48
[52] U.S. Cl. ........................................ 210/695; 210/222; 435/7.92; 436/18; 436/177; 436/526; 514/557
[58] Field of Search ................. 210/222, 223, 695; 252/408.1; 435/7.9, 7.92; 436/18, 177, 526; 514/557

[56] References Cited

U.S. PATENT DOCUMENTS

| | | | |
|---|---|---|---|
| 3,567,026 | 3/1971 | Kolm | 210/222 |
| 3,676,337 | 7/1972 | Kolm | 210/222 |
| 3,902,994 | 9/1975 | Maxwell et al. | 209/213 |
| 3,970,518 | 7/1976 | Giaever | 210/222 |
| 4,018,886 | 4/1977 | Giaever | 210/222 |
| 4,141,687 | 2/1979 | Forrest et al. | 23/230 |
| 4,230,685 | 10/1980 | Senyei et al. | 210/222 |
| 4,267,234 | 5/1981 | Rembaum | 428/403 |
| 4,375,407 | 3/1983 | Kronick | 436/526 |
| 4,452,773 | 6/1984 | Molday | 210/695 |
| 4,554,088 | 11/1985 | Whitehead et al. | 436/526 |
| 4,659,678 | 4/1987 | Forrest et al. | 436/512 |
| 4,663,029 | 5/1987 | Kelland et al. | 209/214 |
| 4,737,294 | 4/1988 | Kukuck | 210/222 |
| 4,784,767 | 11/1988 | Hasuda et al. | 210/222 |
| 4,795,698 | 1/1989 | Owen et al. | 436/526 |
| 4,855,045 | 8/1989 | Reed | 210/222 |
| 4,895,650 | 1/1990 | Wang | 210/222 |
| 4,910,148 | 3/1990 | Sorensen et al. | 210/222 |
| 4,935,147 | 6/1990 | Ullman et al. | 210/222 |
| 4,988,618 | 1/1991 | Li et al. | 210/695 |

FOREIGN PATENT DOCUMENTS

| | | | |
|---|---|---|---|
| 0030087 | 6/1981 | European Pat. Off. | 436/526 |
| 0149565 | 7/1985 | European Pat. Off. | 436/526 |
| 60-177265 | 9/1985 | Japan | 436/526 |
| WO/8706345 | 10/1987 | PCT Int'l Appl. | 436/526 |
| 1578396 | 11/1980 | United Kingdom | 210/222 |

OTHER PUBLICATIONS

Immunoassays for Clinical Chemistry, pp. 147–162, Hunter et al. editors.
The Properties of Magnetic Supports in Relation to Immobilized Enzyme Reactors, Robinson et al., Biotechnology and Bioengineering, vol. XV (1973).
The Dynal MPC-1 (manufactured by DYNAL, Inc., Great Neck N.Y.)—product information sheet (1987).
BioMag Separator (manufactured by Advanced Magnetics, Inc., Cambridge, Mass.)—catalog pages (4 sheets).
Magnetic Separator (manufactured by Ciba-Corning
(List continued on next page.)

Primary Examiner—Robert A. Dawson
Assistant Examiner—Matthew O. Savage
Attorney, Agent, or Firm—Dann, Dorfman, Herrell and Skillman

[57] ABSTRACT

Magnetic separation apparatus and methods for separating colloidal magnetic particles from a non-magnetic test medium in which the magnetic particles are suspended. The separator comprises a container holding the non-magnetic test medium, one or more magnetic wires disposed substantially within the test medium in the container and an external magnet for producing a magnetic field gradient within the test medium. According to the method of the invention, the container holding the test medium is positioned in the separator, producing a magnetic field gradient operative to cause the magnetic particles to be attracted to the areas surrounding the magnetized wires and to adhere to the wires. The non-magnetic test medium is separated from the magnetized particles, which may conveniently be washed while adhered to the wires, and subjected to further analysis, preferably while on the wires. The apparatus and method are useful in separating various target substances from test media by means of substances coated on the magnetic particles which bind specifically to the target substance. A modified buffer solution, when added to the test medium, reduces non-specific binding of the magnetic colloid particles to cells.

42 Claims, 4 Drawing Sheets

OTHER PUBLICATIONS

Medical Diagnostics, Wampole, Mass.)–catalog cover and catalog pages (2 sheets).

Magnetic Separator System (manufactured by Serono diagnostics, Norwell, Mass.)–catalog pages (1 sheet).

Magnetic Separator (made by Miltery Biotech GmbH, Gladbach, Germany)–product information literature.

High Gradient Magnetic Separation Theory and Applications, R. R. Oder, IEEE Transactions on Magnetics, vol. MAG-12, No. 5, Sep. 1976.

Magnetite-Protein Conjugates for the Separation of Cells by High Gradient Magnetic Filtration, C. S. Owen et al., Cell Separation Methods and Selected Applications, vol. 4, 1987.

Magnetic Separation Techniques: Their Application to Medicine J. T. Kemshead et al., Molecular and Cellular Biochemistry 67. 11-18 (1985).

Magnetic Solid-Phase Radioimmunoassay, L. S. Hersh et al., Clinica Chimica Acta, 63 (1975) 69-72.

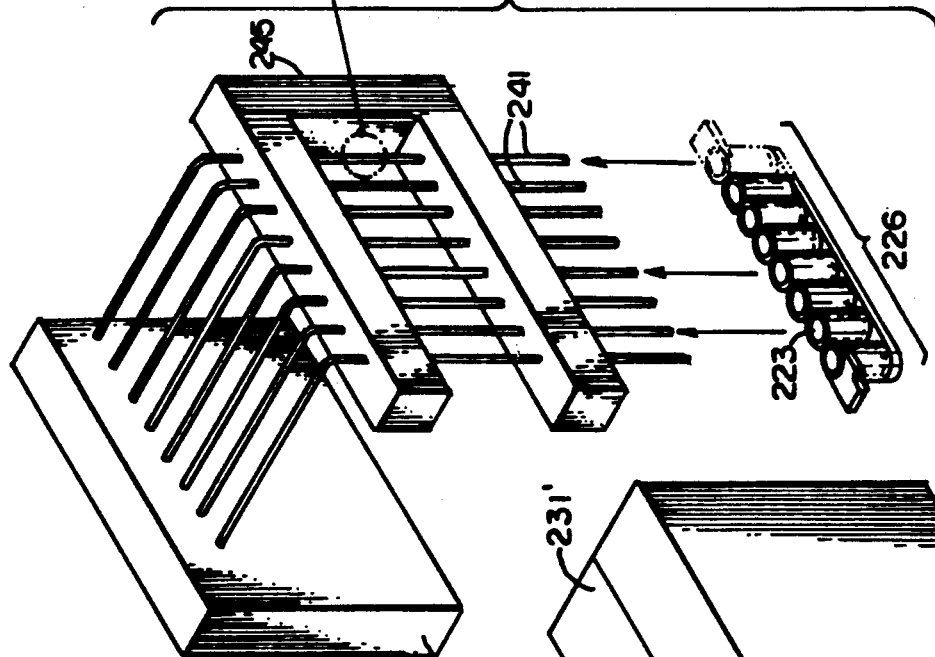

APPARATUS AND METHODS FOR MAGNETIC SEPARATION

FIELD OF THE INVENTION

The present invention is directed to magnetic separation apparatus and methods in which magnetic particles are used for isolating substances of interest from a non-magnetic test medium by means of high gradient magnetic separation (HGMS).

BACKGROUND OF THE INVENTION

The present invention relates to improvements in magnetic separators and methods of separation of magnetic particles from non-magnetic media, having particular utility in various laboratory and clinical procedures involving biospecific affinity reactions. Such reactions are commonly employed in testing biological samples, such as blood or urine, for the determination of a wide range of target substances, especially biological entities such as cells, proteins, nucleic acid sequences, and the like.

As used herein, the term "target substance" refers to any member of a specific binding pair, i.e., a pair of substances or a substance and a structure exhibiting a mutual affinity of interaction and includes such things as cell components, biospecific ligands and receptors. "Ligand" is used herein to refer to substances, such as antigens, haptens and various cell-associated structures, having at least one characteristic determinant or epitope, which are capable of being biospecifically recognized by and bound to a receptor. "Receptor" is used herein to refer to any substance or group of substances having a biospecific binding affinity for a given ligand, to the substantial exclusion of other substances. Among the receptors determinable via biospecific affinity reactions are antibodies (both polyclonal and monoclonal), antibody fragments, enzymes, nucleic acids, Clq and the like. The determination of any member of a biospecific binding pair is dependent upon its selective interaction with the other member of the pair.

Various methods are available for determining the above-mentioned target substances based upon complex formation between the substance of interest and its specific binding partner. Means are provided in each instance whereby the occurrence or degree of target substance/binding partner complex formation is determinable.

In the case of a competitive immunoassay to determine antigen, for example, the antigen of interest in a test sample competes with a known quantity of labelled antigen for a limited quantity of specific antibody binding sites. Thus, after an appropriate reaction period the amount of labelled antigen bound to specific antibody is inversely proportional to the quantity of antigen in the test sample. Competitive assays for antibodies, employing labeled antibodies (typically monoclonal antibodies) rather than labeled antigen, function in an analogous manner. The resulting immune complexes are separated, for example, by immunoabsorption, physico-chemical adsorption or precipitation of either the complexes or unbound antigen. Antibody-bound labeled antigen is then quantified and a standard curve is constructed from known antigen concentrations, from which unknown concentrations of antigen may be determined.

In contrast, immunometric assays for the determination of antigen, commonly known as "sandwich" assays, involve the use of labeled antibodies instead of labelled analyte. In performing an immunometric assay, a sandwich is formed in which the "layers" are: antibody/multivalent (minimally bivalent) antigen/antibody. The amount of labeled antibody which is bound for each complete sandwich complex (antibody/antigen/antibody) is directly proportional to the amount of target antigenic substance present in the test sample. Sandwich assays can be performed in multi-step fashion with polyclonal antibodies or in fewer steps when monoclonals directed to independent antigenic determinants are employed.

In both the conventional competitive immunoassay and the immunometric assay just described, quantitation of the target substance requires a physical separation of bound from free labeled ligand or labeled receptor.

Bound/free separations may be accomplished gravitationally, e.g., by settling, or, alternatively, by centrifugation of finely divided particles or beads coupled to the target substance. If desired, such particles or beads may be made magnetic to facilitate the bound/free separation step. Magnetic particles are well known in the art, as is their use in immune and other bio-specific affinity reactions. See, for example, U.S. Pat. No. 4,554,088 and *Immunoassays for Clinical Chemistry* pp. 147-162, Hunter et al. eds., Churchill Livingston, Edinborough (1983). Generally, any material which facilitates magnetic or gravitational separation may be employed for this purpose.

Small magnetic particles have proved to be quite useful in analyses involving biospecific affinity reactions, as they are conveniently coated with biofunctional polymers, e.g., proteins, provide very high surface areas and give reasonable reaction kinetics. Magnetic particles ranging from 0.7-1.5 microns have been described in the patent literature, including, by way of example, U.S. Pat. Nos. 3,970,518; 4,018,886; 4,230,685; 4,267,234; 4,452,773; 4,554,088; and 4,659,678. Certain of these particles are disclosed to be useful solid supports for immunologic reagents, having reasonably good suspension characteristics when mildly agitated. Insofar as is known, however, absent some degree of agitation, all of the magnetic particles presently in commercial use settle in time and must be resuspended prior to use. This adds another step to any process employing such reagents.

Small magnetic particles, such as those mentioned above, generally fall into two broad categories. The first category includes particles that are permanently magnetized; and the second comprises particles that become magnetic only when subjected to a magnetic field. The latter are referred to herein as magnetically responsive particles. Materials displaying magnetically responsive behavior are sometimes described as superparamagnetic. However, certain ferromagnetic materials, e.g., magnetic iron oxide, may be characterized as magnetically responsive when the crystal is about 300A or less in diameter. Larger crystals of ferromagnetic materials, by contrast, retain permanent magnet characteristics after exposure to a magnetic field and tend to aggregate thereafter. See P. Robinson et al., *Biotech Bioeng.* XV:603-06 (1973).

Magnetically responsive colloidal magnetite is known. See U.S. Pat. No. 4,795,698 to Owen et al., which relates to polymer-coated, sub-micron size magnetite particles that behave as true colloids.

The magnetic separation apparatus/method used for bound-free separations of target substance-bearing magnetic particles from test media will depend on the nature and particle size of the magnetic particle. Micron size ferromagnetic, i.e, permanently magnetized, particles are readily removed from solution by means of commercially available magnetic separation devices, employing relatively inexpensive permanent magnets. Examples of such magnetic separators are the MAIA Magnetic Separator manufactured by Serono Diagnostics, Norwell, Mass. the DYNAL MPC-1 manufactured by DYNAL, Inc., Great Neck, N.Y. and the BioMag Separator, manufactured by Advanced Magnetics, Inc., Cambridge, Mass. A similar magnetic separator, manufactured by Ciba-Corning Medical Diagnostics, Wampole, Mass. is provided with rows of bar magnets arranged in parallel and located at the base of the separator. This device accommodates 60 test tubes, with the closed end of each tube fitting into a recess between two of the bar magnets.

The above-described magnetic separators have the disadvantage that the magnetic particles tend to form several layers on the inner surface of the sample container where they are entrapped along with impurities that are difficult to remove even with vigorous washing.

Colloidal magnetic materials are not readily separable from solution as such, even with powerful electro-magnets but, instead, require high gradient field separation techniques. See, R.R. Oder, *IEEE Trans. Magnetics*, 12:428-35 (1976); C. Owen and P. Liberti, *Cell Separation: Methods and Selected Applications*, Vol. 5, Pretlow and Pretlow eds., Academic Press, N.Y., (1986). The gradient fields normally used to filter such materials generate huge magnetic forces. Another useful technique for performing magnetic separations of colloidal magnetic particles from a test medium, by various manipulations of such particles, e.g., addition of agglomerating agents, is the subject of co-pending and commonly owned U.S. Pat. application Ser. No. 389,697, filed Aug. 4, 1989.

A commercially available high gradient magnetic separator is the MACS device made by Miltenyi Biotec GmbH, Gladbach, West Germany, which employs a column filled with a non-rigid steel wool matrix in co-operation with a permanent magnet. In operation, the enhanced magnetic field gradient produced in the vicinity of the steel wool matrix attracts and retains the magnetic particles while the non-magnetic test medium passes through and is removed from the column.

It has been found that the steel wool matrix of such prior art HGMS devices often gives rise to non-specific entrapment of biological entities other than the target substances which cannot be removed completely without extensive washing and resuspension of the particles bearing the target substance. Moreover, the size of the column in many of the prior art HGMS devices requires substantial quantities of experimental materials, which pose an impediment to their use in performing various useful laboratory-scale separations. In addition, the steel wool matrix may be harmful to certain sensitive cell types.

Although HGMS affords certain advantages in performing medical or biological analyses based on biospecific affinity reactions involving colloidal magnetic particles, the systems developed to date have not been entirely satisfactory for the above-mentioned reasons. Accordingly, it would be desirable to provide HGMS apparatus and methods which are of relatively simple construction and operation and yet maximize magnetic field gradients, and which reduce entrapment of non-target substances, eliminate loss of immobilized target substance due to shear forces or collisions with other biological entities, and employ standard microtiter plate wells, and the like, so as to be of practical utility in conducting various laboratory-scale separations, particularly in immunoassays and cell sorting.

SUMMARY OF THE INVENTION

It is an object of this invention to provide magnetic separation apparatus and methods capable of generating a high gradient magnetic field within the test medium to separate magnetically responsive colloidal particles from a non-magnetic test medium. Unlike relatively larger size magnetic particles which tend to settle out of the test medium, magnetically responsive colloidal particles remain suspended in a test medium for an indefinite period, thereby making them readily accessible to target substances.

The magnetic separator of the invention comprises at least one test container, a magnetic field gradient intensifying means, preferably in the form of one or more rigid ferromagnetic elements disposed within the test container, and magnetic means external to the container for generating a magnetic field intersecting the ferromagnetic elements within the test container. The container preferably is non-magnetic and has an opening for receiving a test medium which contains magnetic particles and provides a chamber for performing the desired separation.

Preferably, the magnetic field generating means comprises a pair of confronting magnets defining a cavity or slot which accommodates a test container and positions the ferromagnetic elements for coaction with the magnetic field produced by the confronting magnets.

The ferromagnetic elements may comprise rigid magnetic wires having one or both ends attached to a carrier positioned outside of the container. In a particularly preferred embodiment for cell separations, both ends of the wire are affixed to the carrier and the wire is formed in the shape of a loop. In another embodiment, the carrier is an annular cap or closure, adapted to be mounted on the container, which has one or more rigid magnetic wires, preferably a multiplicity of wires, descending from the under side of the cap so that the wires are disposed within the container when in use.

In another preferred embodiment, the magnetic field intensifying means may take the form of a wire screen adapted to be mounted in a fixed position within the container. The wire screen may take any shape. Preferred forms of the screen include a triangularly shaped body open at both ends, and a hollow cylinder also open at both ends.

The physical properties of the magnetic particles preferably used in the practice of this invention, particularly their relatively small particle size, permit a level of operating efficiency which, insofar as is known, has not been achievable heretofore. Furthermore, by controlling the quantity of magnetic particles added to the test medium, relative to the exposed surface area of the magnetic field intensifying means, and controlling the orientation of such exposed surface, so as to be substantially transverse to the magnetic field, it is possible to cause the magnetic particles to adhere to the surface of the magnetic field intensifying means in a substantially single layer, corresponding in thickness to about the size of the target substance-bearing magnetic particles. Occlusion of non-specifically bound substances by the trapped magnetic particles is virtually negligible.

In separating magnetic particles from non-magnetic components of a test medium in accordance with the method of the invention, magnetic particles are dispersed in the test medium forming a stable suspension therein. The magnetic particles comprise a receptor capable of specific binding to the target substance of interest in the test medium. One or more containers holding the test medium, the receptor-magnetic particle conjugates and the magnetic field intensifying means are placed in the magnetic separator, with the magnetic field intensifying means immersed substantially within the test medium. The separator brings an external magnetic field to bear on the container, producing a magnetic field gradient in the test medium, which causes the magnetic particles to be attracted toward the magnetic field gradient intensifying means and to become adhered thereto. Thereafter, the non-magnetic test medium may be removed from the separator while the magnetic particles are retained on the wires and are subjected to further processing, as desired. By performing analyses involving biospecific affinity reactions in this way, resuspension of the magnetic particles bearing the target substance is effectively obviated. Accordingly, this method substantially reduces the processing time required for, and thus the cost of, bioanalytical testing.

It is also an object of this invention to provide a composition of matter which facilitates the method of the invention by reducing the occurrence of non-specific binding due to uncoated surface portions of the transition metal oxides comprising the magnetic particles. The composition of the invention comprises an anionic polyelectrolyte and a physiologically compatible carrier.

From the foregoing summary, it will be appreciated that the present invention provides separation apparatus and methods of relatively simple construction and operation which enable the efficient and effective separation of target substance-bearing magnetic particles from a test medium.

BRIEF DESCRIPTION OF DRAWINGS

FIG. 8 is a perspective view of yet another embodiment of the invention, utilizing a plurality of capillary tubes as separation chambers;

FIG. 8A is an enlarged cross-sectional view of a portion of a capillary tube with a wire filament disposed therein as a magnetic field gradient intensifier.

Like characters of reference designate like parts in those figures of the drawings in which they occur.

DESCRIPTION OF PREFERRED EMBODIMENTS

Figure 1:
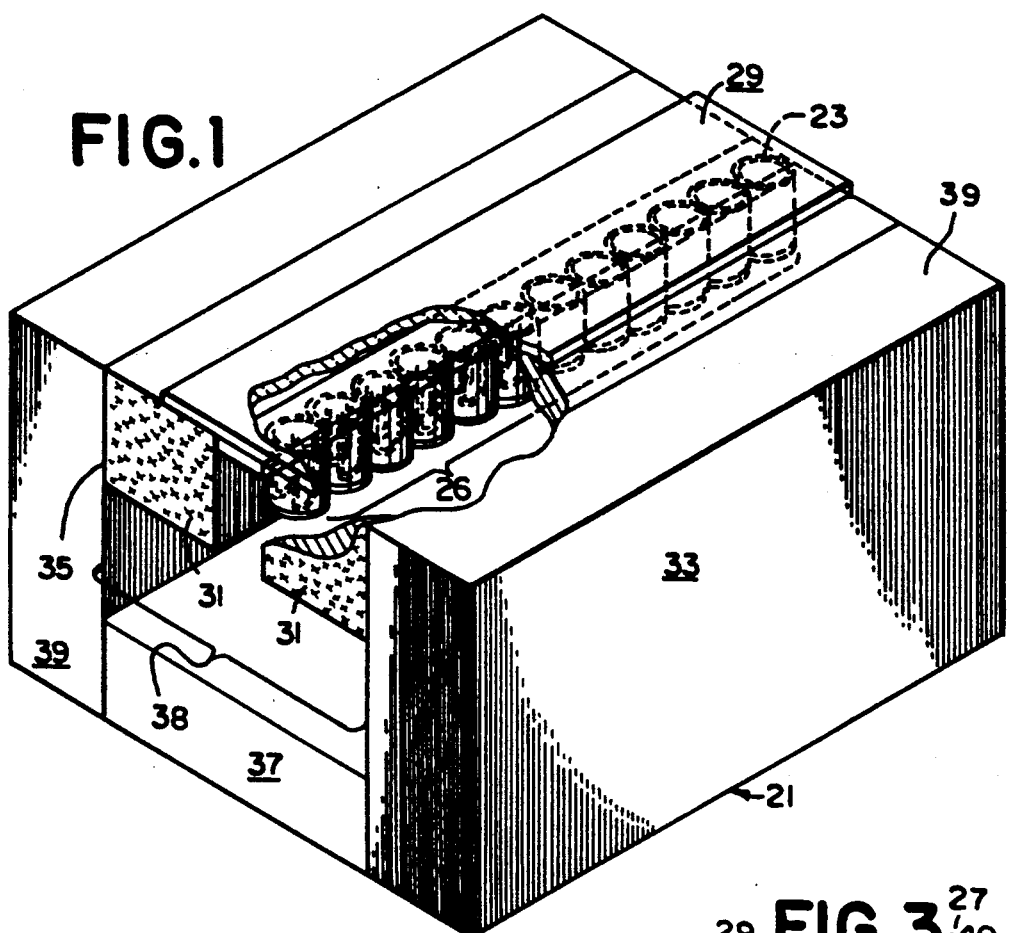
FIG. 1 is a perspective view of a magnetic separation apparatus embodying the present invention, portions of the apparatus being broken away for the purposes of illustration.

Preferred embodiments of the present apparatus and methods will now be described in detail with reference to the drawings.

The magnetic separation apparatus and methods of the present invention have particular utility in various laboratory and clinical procedures involving biospecific affinity reactions. In such procedures, particles are used which are at once magnetically responsive and colloidal (i.e., particles which are superparamagnetic and capable of remaining in suspension in a non-magnetic test medium), and which comprise a receptor capable of binding the substance of interest in the test sample. In the present method, after the receptor binds the target substance, the magnetic separator removes the magnetic particles from the test medium via HGMS.

Such biospecific affinity reactions may be employed in testing biological samples for the determination of a wide range of target substances, representative of which are cells, cell components, cell subpopulations (both eucaryotic and procaryotic), bacteria, parasites, antigens, specific antibodies, specific biological factors, such as vitamins, viruses and specific nucleic acid sequences, as in the case of gene probe analysis. Thus, the magnetic separation apparatus and method of the invention may be used to carry out cell separations for the analysis or isolation of cells including, by way of example: T-cells from a T-cell lymphoma cell line; B-cells from a B-cell lymphoma cell line; CD4 positive cells from leukocytes; and lymphocytes from leukocytes.

The methods of the invention may also be used for immunospecific isolation of monocytes, granulocytes and other cell types; removal of rare cells; depletion of natural killer cells; determination of reticulocytes; and assays for neutrophil function, e.g., for determining changes in membrane potential, performing oxidative burst analysis, phagocytosis assays and opsonization studies.

Similarly, the present magnetic separation apparatus and method may be used in bacterial or parasite separation or analysis, including the separation of various bacteria and parasites from fecal matter, urine, sludges, slurries and water (e.g., ground water or streams). The present invention may also be used in separating various bacteria in food products (liquids to solids) sputum and urine.

The preferred magnetic particles for use in carrying out this invention are particles that behave as true colloids. Such particles are characterized by their submicron particle size, which is generally less than about 200 nanometers (nm.) (0.20 microns) and their stability to gravitational separation from solution for extended periods of time. Suitable materials are composed of a crystalline core of superparamagnetic material surrounded by molecules which may be physically absorbed or covalently attached to the magnetic core and which confer stabilizing colloidal properties. The size of the colloidal particles is sufficiently small that they do not contain a complete magnetic domain, and their Brownian energy exceeds their magnetic moment. As a consequence, North Pole, South Pole alignment and subsequent mutual attraction/repulsion of these colloidal magnetic particles does not appear to occur even in moderately strong magnetic fields, contributing to their solution stability. Accordingly, colloidal magnetic particles are not readily separable from solution as such even with powerful electromagnets, but instead require a magnetic gradient to be generated within the test medium in which the particles are suspended in order to achieve separation of the discrete particles.

Magnetic particles having the above-described properties can be prepared as described in U.S. Pat. No. 4,795,698, the entire disclosure of which is incorporated by reference in the present specification, as if set forth herein in full.

For cell separations, the test medium is typically prepared from appropriately prepared body fluids, such as blood, urine, sputum or secretions. It is preferable to add the colloidal magnetic particles to the test medium in a buffer solution. A suitable buffer solution for this purpose comprises a mixture of 5% bovine serum albumin ("BSA") and 95% of a biocompatible phosphate salt solution, optionally including relatively minor amounts of dextrose, sodium chloride and potassium chloride. The buffer solution should be isotonic, with a pH about 7. The protein serves to decrease interactions which tend to interfere with the analysis. The target substance may be added to the test medium before, after or simultaneously with introduction of the magnetic particles. The method of the invention takes advantage of the diffusion controlled solution kinetics of the colloidal magnetic particles, which may be further enhanced by the addition of heat to the test medium. The test medium is usually incubated to promote binding between the receptor and any ligand of interest present therein. Incubation is typically conducted at room temperature or at a temperature slightly above the freezing point of the test medium (i.e., 4° C.). The period of incubation is normally of short duration (i.e., about 15 minutes). The test medium may be agitated or stirred during the incubation period to facilitate contact between the receptor and ligand.

It has been discovered that if a small percentage of the buffer solution is replaced by a suitable anionic polyelectrolyte, binding of the receptor to a material other than the target substance in the test medium (i.e., non-specific binding) is reduced. Satisfactory results have been obtained using a commercial scale inhibitor sold under the name Tamol 850, which is available from Rohm and Haas, Philadelphia, Penna. Tamol 850 is sold as an aqueous solution of polymethacrylic acid, having a molecular weight of 12,000 (weight average), total solids of 29-31%, density of 9.9 lbs./gal. (at 25° C.), a Brookfield viscosity of 125-325 (at 25° C.) and a spindle/speed of #2 @60. The addition of about 0.1% to about 3% Tamol 850 (on an active basis) to the phosphate buffer will generally be adequate to reduce non-specific binding in the practice of this invention. This buffer composition and its use in reducing non-specific binding are also within the scope of the present invention.

After binding of the receptor to the substance of interest is allowed to occur, magnetic separation of the colloidal magnetic particles from the test medium is performed using the apparatus and methods of the present invention. The test medium is disposed in a container which is subjected to an externally applied magnetic field, whereby a magnetic flux is generated within the test medium. In accordance with a preferred embodiment of the invention, magnetic wires are immersed in the test medium to enhance the magnetic field gradient, so as to cause the magnetic particles to migrate toward the surface of the magnetic wire to which they adhere, rendering them easily separable from the test medium.

FIGS. 1-4 illustrate an embodiment of a magnetic separator in accordance with the present invention. The separator 21 has an array 26 of twelve containers 23 and a pair of wire loops 25 inserted into each container. The ends 27 of each loop are attached to a carrier 29. The magnetic separator also has a pair of confronting magnets 31 that are positioned on opposite sides of the array of containers.

As shown in FIG. 1, the container used to hold the test medium may be cylindrical in shape with an open top. In the illustrated embodiment, each container 23 is a microtiter well, and twelve wells are interconnected, for example by a weld or other connection at 24 to form an array 26. All of the wells may be used concurrently in the present method, thus permitting many separations of magnetic particles from test media to be carried out simultaneously or sequentially, as desired. Preferably, the interconnections 24 in the array 26 are made, so that individual wells may be separated from the array without difficulty to facilitate individual test sample handling, if desired. The interconnections 24 in the array may be accomplished by virtually any means, such as by molding the array as one piece with score lines or other weakened areas facilitating separation, or by the use of releasable connectors or by suitable adhesives. The array of interconnected containers may be of any number including single containers or shaped tubes, such as capillary tubes that are capable of being accommodated by the magnetic separator.

In the embodiment of FIGS. 1-4, magnetic field gradient enhancement is achieved by the wires 25 formed into pairs of semi-ovate loops which are separated within each container and substantially immersed in the test medium. To this end, the ends of the wires forming the loops 25 are anchored in carrier 29, which is positioned outside of the test medium.

Wires made from any of various ferromagnetic materials may be employed in the magnetic separator. The wire may be of greater diameter than standard gauge wire, preferably having a diameter of between about 0.8 mm. and 3.0 mm. Such relatively thick wire is less likely to deform when entering and leaving the magnetic field or when in non-homogeneous regions that may exist within the magnetic field. Moreover, the wire provides an ample surface area for adherence of the colloidal magnetic particles. An advantage of the magnetic separator of the invention, when utilized under the conditions described above, is that by appropriately regulating the quantity of colloid, the particles tend to deposit substantially uniformly upon surfaces in contact with the medium where the magnetic gradient is high. As a result, particles are deposited on a broad portion of the surface of the wire in what is effectively a single layer, as opposed to multiple layers or aggregates of particles forming on a smaller surface, such as occurs with magnetic separators of the prior art. The deposition of a single layer of particles substantially reduces the problem of entrapping impurities or other interfering substances on the wire and occluded within an aggregate of target substance-bearing magnetic particles. For this reason, it is preferable that the size of the wires in contact with the test medium be selected so that their aggregate collecting surface area is greater, by a factor of about 2, than the surface area that would be occupied by all of the magnetic particles in the test medium, if disposed in a substantially continuous single layer.

Figure 3:
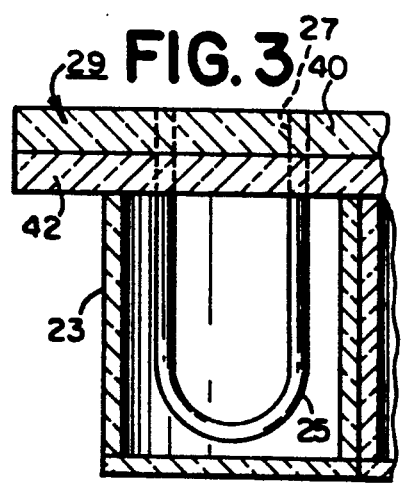
FIG. 3 is a fragmentary longitudinal sectional view of the apparatus shown in FIG. 1.

The carrier 29 shown in FIGS. 1 and 3 is preferably non-magnetic and transparent. The carrier supports the wires in a fixed position and also serves as a cover over the open top of containers 23. The carrier may be fabricated from various materials, plexiglass ® being preferred. Alternatively, instead of anchoring both ends of a wire in the form of a loop, the holder may support only one end of a wire. The wire or wires may assume virtually any shape that satisfies the condition that the wires are capable of being substantially immersed within the test medium. The wires may be single or multiple strands, but should be arranged so that the collecting surfaces of adjacent strands do not form capillaries, pockets or interstices which might entrap non-magnetic components of the test medium.

As shown in FIG. 1, the means for generating a magnetic flux in the test medium comprises two magnets 31 which confront each other with the array 26 of interconnected containers 23 positioned in a slot or cavity defined by the confronting magnet surfaces. The magnetic field strength of the external magnetic device should be in a range of between about 4 kGauss and about 15 kGauss, and more preferably between about 7 KGauss and about 8.5 kGauss. The preferred distance between each magnet and the array of containers shown in FIG. 1 is about 0.5 cm. to about 2.5 cm. with the most preferable distance being about 1 cm. The field strength of the external magnet or magnets should be great enough and the distance between the magnets 31 and the container 23 holding the test medium should be short enough to induce high field gradients by means of the magnetic wires 25 within the container. The wire loops 25 are preferably oriented so that the direction of the magnetic field of the external magnets 31 is substantially transverse to the longitudinal axes of the wires, thereby optimizing the magnetic field gradient within the test medium.

The confronting magnets 31 are mounted along one side 35 of each magnet within a U-shaped support structure 33. The structure has a base 37 and two parallel sides 39, each side being connected to the base. The space 38 between the sides 39 above the base 37 provides room to enable manipulation of the array 26. For example, an elevating mechanism (not shown) may be positioned in the space 38 to raise and support the array 26 in the position illustrated.

The carrier 29 closes space 38 and comprises a cross piece 40 which rests upon the magnets 31 above the space 38. On the underside of the cross piece 40 a centering plate 42 is positioned to fit between the confronting face of the magnets, so as to center the loops within the slot between the faces of the magnets 31. If desired, the downwardly-facing surface of the centering plate 42 may be contoured to mate with the cylindrical wall of the container to cap the same when the array is elevated to the position shown in FIG. 3.

Figure 2:
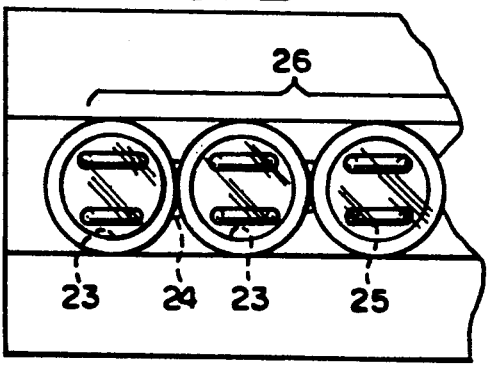
FIG. 2 is a fragmentary inverted plan view of the apparatus shown in FIG. 1.
Figure 4:
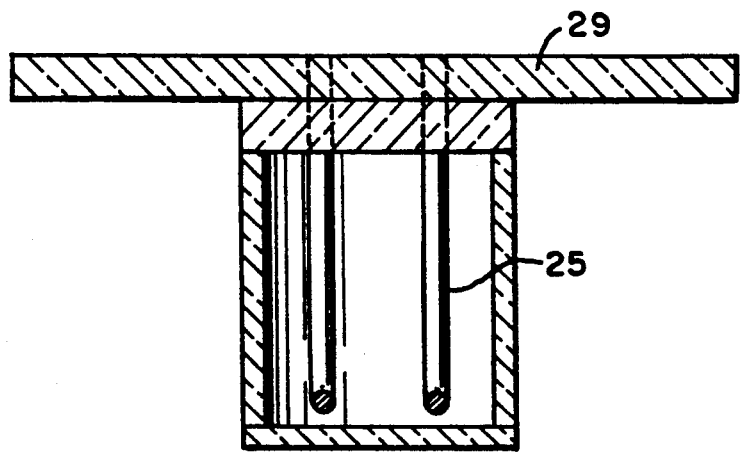
FIG. 4 is a transverse sectional view similar to the longitudinal sectional view of FIG. 3.

FIGS. 2-4 show a preferred form of the wire loops in the container. The loops should not touch an inner wall of the container in order to avoid trapping of the target substance between the loops and the wall. In addition, the loops are preferably equidistant from each other and from the walls to maximize the distance between the magnetic particles on a surface of each loop and the magnetic particles on the closest surface of the nearest loop.

Figure 5:
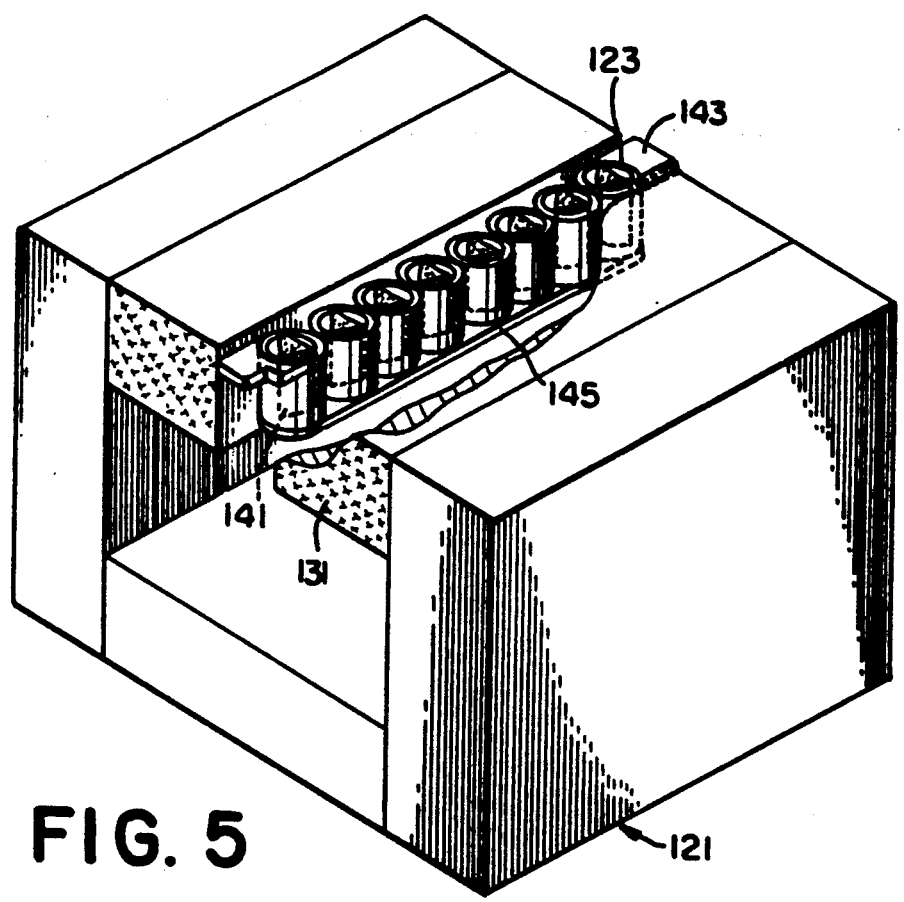
FIG. 5 is a perspective view of another embodiment of the invention.

FIG. 5 illustrates another embodiment of the magnetic separator of the invention that is similar to the magnetic separator shown in FIG. 1. The separator 121 shown in FIGS. 5, 6 and 7 employs an array 126 of eight interconnected containers 123 containing an alternative field gradient intensifier means and confronting magnets 131 on each side of the array 126 of containers. In this embodiment, the containers are hollow cylindrical members mounted on a base 124 which serves as a bottom for each container 123 and also serves as a connector for interconnecting the adjacent containers in the array. If desired, the base may be scored or provided with weakened lines (not shown) intermediate the containers to enable separation of the individual containers. A magnetic wire screen 141 is positioned in each container to enhance the density of the magnetic flux therein.

Screen 141 is preferably woven from ferromagnetic wires to provide a porous sheet-like member which is formed into a hollow triangularly shaped body open at both ends. The triangular shape of the screen provides rigidity to the screen although other shapes may be used, such as a hollow cylinder open at both ends. Each wire screen 141 is further dimensioned to be mounted in a fixed position within the container 123. Preferably, the triangular body is fitted against the cylindrical wall of the container 123 and is held in place by friction in such a way to avoid entrapment of non-magnetic components of the test medium.

The wires of the screen are positioned so that the magnetic field intercepts the wires in the screen transverse to their respective longitudinal axes. In addition, the hollow space in the triangular body allows measurements (i.e., of light absorption) to be taken of the test medium while the screen remains in place. Preferably, the top of the screen is level with the top of the container to facilitate removal of droplets of test medium from the screen that remain after the test medium has been removed from the container.

Figure 6:
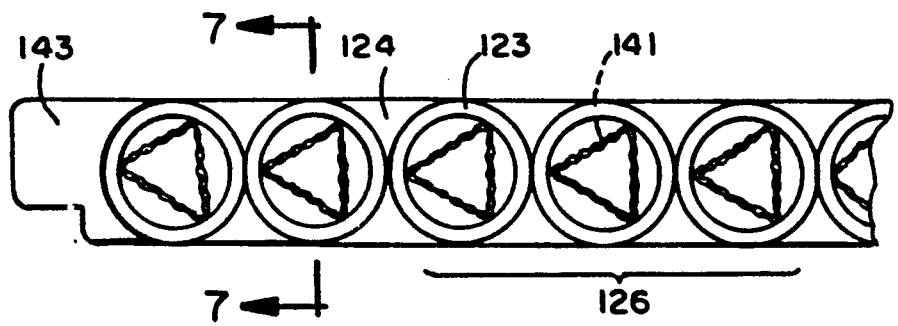
FIG. 6 is a fragmentary plan view showing the test medium container used in the embodiment of the invention shown in FIG. 5.
Figure 7:
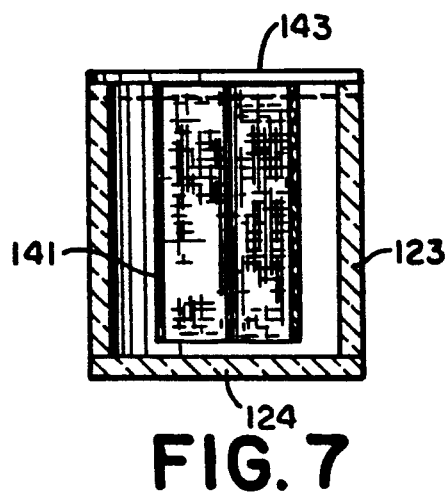
FIG. 7 is a sectional view taken on the line 7—7 of FIG. 6.

As shown in FIG. 6, the array 126 of containers 123 has tabs or end pieces 143 that may be adapted to fit into slots in the separator support structure (not shown) to provide a support for the containers in the separator. Alternatively, the containers may rest on the platform of an elevator device (not shown) to be raised or lowered into and out of the space between the magnets 131.

FIG. 8 illustrates a further embodiment of the magnetic separator of the invention which utilizes an array of capillary tubes 241 which serve as separation chambers for conveniently performing a number of immunoassays simultaneously. A 10 cm by 0.025 cm magnetic wire is positioned within each capillary tube as the field gradient intensifier means. An array 226 of interconnected containers or wells 223 is provided to collect the test media discharged from the tubes for analysis. The capillary tubes are mounted in a frame 245 for registry with each container. A suitable supply unit 248 is provided which operates to pump into each capillary tube a preformulated test medium including all of the reagents needed for forming labeled immune complexes. The supply unit also delivers to the capillary tubes other reagents used in performing the assay. Block magnets 231, 231' are assembled with a suitable spacing therebetween so as to easily engage and disengage frame 245. The magnetic wire within the capillary tubes 241 is preferably ferromagnetic to enhance the magnetic field gradient within the capillary tube upon application of an external magnetic field.

To effect separation of the magnetic particles from the test medium using the magnetic separator apparatus of FIG. 1, the container array 26 may be lowered away from carrier 29 after the test medium has been subjected to the magnetic field for a sufficient time to cause the magnetic particles to migrate and adhere to loops 25. The particles will remain adhered to the loops and the non-magnetic components of the test media will be removed with the containers. A similar array 26 of containers containing a buffer, a rinse, or other fresh solution may then be elevated into place to immerse the loops in the fresh solution for rinsing purposes. The loops are placed in the fresh solution to dislodge any residual non-magnetic components by rinsing. If desired, the rinse solution may be removed and the process may be repeated with a liquid reagent. If it is desired to suspend the magnetic particles in the liquid reagent, the loops and the array of containers may be removed from the magnetic field and be manipulated to allow the magnetic particles to be dislodged from the wires and suspended in the liquid reagent, e.g., to facilitate analysis. Alternatively, the fresh array may serve as collection medium without the presence of a liquid reagent.

A similar collection procedure may be followed using the magnetic separator shown in FIG. 5. In such case, after the array of containers 126 is removed from the magnetic field, the separated magnetic particles may be dislodged from each screen and collected in the bottom of the container. If desired, the triangular screen bodies may be removed from the containers to facilitate further treatment or analysis of the particles.

The ability to retain the magnetic particles adhered to the magnetic gradient-intensifying wire after the test medium has been removed is of considerable utility. Certain operations are more efficiently carried out in this way, such as washing or rinsing the target substance, e.g., cells or labeled components of a reaction mixture, while avoiding a separate resuspension step. In addition, secondary reactions such as those involving the interaction of labeled immunoreactive agents with the target substance on the magnetic particles may be performed more efficiently with the particles adhered to the wire. Here again, resuspension of the colloidal magnetic particles may be avoided. Furthermore, in performing enzyme-labelled immunoassays in accordance with the present invention, substrate incubation is preferably carried out on the immobilized colloidal magnetic particles. This approach permits advantageous use of diffusion controlled solution kinetics of the primary incubation mixture. Thereafter, various analytical procedures, including quantitative determinations, may be performed on the magnetically immobilized coloid. Such steps include washes for removal of non-specifically bound substances, secondary immunochemical reactions and detection reactions (e.g., enzymatic, fluorescent or chemiluminescent reactions).

Performing the magnetic separation method of the invention batchwise or in a steady-state system, as described above, instead of in a flow through system, has certain advantages. Immobilized magnetic particles bearing the target substance are not dislodged due to collisions with other particles. Moreover, batchwise operation eliminates dislodgment of immobilized magnetic particles due to shear forces produced by a flowing test medium. In other words, the adherence of the magnetic particles to the wire is sufficiently strong to permit washing, secondary reactions, and interactions with other reagents to occur without appreciable dislodgement of the magnetic particles from the wire. In addition, the adherence of the magnetic particles to the wire is maintained to some extent even if the wire is removed from the magnetic field before further reaction with, or treatment of the particles.

In general, the magnetic particles are relatively easily separated from the wire after removal from the magnetic field. The particles may be separated by contacting the wire with a modified buffer solution, or a bath sonicator. Alternatively, the particles may be collected as they are dislodged from the wire with a probe sonicator, or oscillating magnetic fields can be employed to demagnetize the ferromagnetic wires as well as create forces on the particles.

The ability to maintain the particles adhered to the wire, or to remove the particles from the wire, as desired, is enhanced greatly by providing a surface coating on the wire. The magnetic particles have a much greater tendency to adhere to an uncoated wire than to a wire coated with a clear or colorless acrylic coating, for example. Any biocompatible coating material that provides the coated wire with a low coefficient of friction may be used in facilitating removal of magnetic particles from the wire.

In using a wire screen to enhance the flux density, the mesh of the screen is selected to provide magnetic attraction of the magnetic particles with minimum retention of the non-magnetic components of the test medium within the interstices of the wire mesh by surface tension. A coating on the wire screen may reduce such surface attraction. In most instances, it is desirable to provide a coating which avoids filling the interstices and reducing or eliminating the porosity of the wire screen element.

The following examples further describe in some detail the manner and process of making and using the present invention and set forth the best mode contemplated by the inventors for carrying out the invention, but are not to be construed as limiting the invention. All temperatures given in the examples are in ° C., unless otherwise indicated.

EXAMPLE 1

A magnetic separator of the general configuration shown in FIG. 1, employing pairs of wire loops, was used to separate colloidal magnetic particles from a test medium. Three batches of magnetic particles were prepared according to the procedure described in Example 1 of U.S. Pat. No. 4,795,698; one having a coating of non-specific protein and each of the other two having a coating of a specific binding protein, to evaluate the relative effectiveness of the resultant colloidal particles in binding a target substance for subsequent separation of the formed colloid/target substance complex. The target substance in this experiment was chromium 51 ("$CR^{51}$") labelled human T-cells (ATCC Accession No. CCL 119 CCRF-CEM). Information regarding appropriate conditions for culturing these cells is available from ATCC. Cell labelling was carried out according to the procedure of G.G.B. Klaus, *Lymphocytes, A Practical Approach*, IRL Press Limited 1987, pg. 144. After labelling and washing the cells as per the above reference, cells were resuspended to approximately $3 \times 10^6$ cells/ml in buffer A, consisting of cell-compatible isotonic PBS with 0.1% sodium azide, pH 7.2, supplemented with 1% (w/v) BSA (hemocytometer used to count cells). Next, the counts per minute ("cpm") per cell were determined by counting an aliquot of the CR[51] labelled cells in a gamma counter.

The non-specific protein coating applied to the magnetic particles was bovine serum albumin ("BSA") and the resultant suspension had a BSA concentration of 1 mg/ml (Colloid No. 11054-1). The first specific-binding protein coated magnetic particles were coated with an affinity purified goat anti-mouse Fc antibody (GAMFc) (Colloid No 08314-1). Colloid No. 08314-1 had an antibody concentration of 1 mg/ml. The second specific-binding protein coated magnetic particles were coated with an affinity purified sheep anti-mouse whole molecule antibody (SAM) (Colloid No. 06064-1). Colloid No. 06064-1 had an antibody concentration of 1 mg/ml.

The non-specific and specific binding colloids which are typically 1 mg/ml iron to start, were diluted in buffer A which had been previously supplemented with 0.5% Tamol 850 (w/v) on an active basis to achieve 0.02 mg/ml iron and 0.02 mg/ml protein (BSA or GAMFc or SAM).

An aliquot (150 ul) of diluted Colloid No. 11054-1 was added to each of four 12×75 mm glass tubes. Aliquots of the same volume of each of diluted Colloid No. 08314-1 and diluted Colloid No. 06064-1 were added separately to each of two tubes of the same dimensions, for a total of eight tubes (tubes 1–4 containing Colloid No. 11054-1; tubes 5 and 6 containing Colloid No. 08314-1; and tubes 7 and 8 containing Colloid No. 06064-1).

Then, 20 ul of the buffer composition of the invention was added to each of tubes 1 and 2 and 20 ul of a monoclonal antibody CD45 10Lib CAT 0646 Lot 1 ("CD45") were added to tubes 3–8. CD45, having a stated expiration date of "11/90", was obtained from AMAC, a divsion of Immunotech, Westbrook, Maine. The contents of tubes 1–8 were incubated for one hour.

Finally, 150 ul of the CR[51]-labelled human T-cells were added to each of tubes 1–8 and the resultant mixtures were incubated for 15 minutes at room temperature followed by 15 minutes at 4° C. The contents of tubes 1–8 were counted using a gamma counter during the 15 minute room temperature incubation. These counts represent the total cpm's for the reaction mixture.

After the 15 minute 4° incubation, an aliquot (250 ul) of the test medium from each of tubes 1–8 was transferred to a separate serially connected set of microtiter wells which were assigned the same identifying numbers. The cpm for the material remaining (70 ul) in the glass reaction tubes was determined using a gamma counter and was subtracted from the total cpm determined above, resulting in a cpm for the 250 ul reaction mixture which was further translated into number of cells per reaction using the cpm/cell number above. Next, a pair of magnetic metal loops were inserted into each of wells 1–8. The two ends of each wire loop were attached to a plastic carrier, as shown in FIG. 1. The microtiter wells with wire loops inserted into the wells as described was then slid into a magnetic device as shown in FIG. 1 which in this case had a field strength of 8–8.5 kGauss, as determined using a Gauss meter with the probe of the meter held in the center of the gap between the opposing magnets. To assist in the above-described procedure of sliding the wells and wire loops into the magnetic device, a wood block was used to support the microtiter wells adjacent to the wire loop carrier, as shown in FIGS. 3 and 4. Under the influence of the magnets, a high gradient magnetic field is generated on the wire loops, thereby causing cells in the test medium, which have colloidal particles attached to their surfaces, to collect on the wire loops.

After a 10 minute exposure to the external magnetic field, wells 1–8 were lowered away from the loops, so that each well then contained only the supernatant from each separation. Facilitated by the use of snap-apart wells, each well was separated and inserted into counting tubes and a gamma counter to determine the cpm remaining in each supernatant which was further translated into the number of cells left in the supernatant using the cpm/cell number as determined above. The percent cell removal or depletion was then calculated knowing the number of cells per reaction and the number of cells per supernatant, as described above, by subtracting the latter from the former, dividing this difference by the former and multiplying by 100.

In this test, after separating the microtiter wells from the wire loop carrier, a wash step was performed on the cells immobilized on the wire loops with the loops (and cells) still in the magnetic field. This was achieved by pipetting 250 ul of buffer A supplemented with 1% (w/v) BSA into 8 new microtiter wells (labelled 1–8), positioning the wells adjacent to the wire loop carrier, such that each set of wire loops from test 1–8 was in contact with the buffer of new wells 1–8. The wells were left in place for 30 seconds, removed from the magnetic field and separated to determine the number of cells removed during the wash step by counting the supernatants as above.

The results of this experiment are set forth in TABLE 1.

TABLE 1

| Well No. | No. of cells in test medium | No. of cells separated on wire loops (no wash) | Percentage of cells separated (no wash) | Percentage of cells separated (one wash) |
| --- | --- | --- | --- | --- |
| 1 | 358,731 | 46,721 | 13.02 | 11.23 |
| 2 | 346,597 | 39,888 | 11.51 | 10.50 |
| 3 | 348,613 | 46,278 | 13.27 | 12.03 |
| 4 | 349,036 | 50,873 | 14.58 | 13.48 |
| 5 | 343,755 | 271,396 | 78.95 | 77.16 |
| 6 | 350,648 | 274,802 | 78.37 | 77.03 |
| 7 | 343,150 | 106,582 | 31.06 | 28.68 |
| 8 | 343,715 | 115,936 | 33.73 | 32.02 |

Referring to Table 1, the separation of over 77% of the target Cr[51] labelled cells in wells 5 and 6 demonstrates the efficiency of the magnetic separation apparatus and method of the invention in removing colloidal magnetic particles from the test medium and the ability of such particles to bind a high percentage of the target substance.

EXAMPLE 2

The magnetic separator described in Example 1 was employed to determine the effect of Tamol 850 as a suitable anionic polyelectrolyte for reducing non-specific binding of colloid particles to human T-cells in the practice of the invention.

It has been discovered, in accordance with the present invention, that the use of polymers, proteins, additives, detergents and like substances, containing a net negative charge, when incorporated into standard cell-biocompatible buffers and used to dilute colloidal magnetic particles, significantly reduces non-specific binding of such colloidal magnetic particles to cells. The non-specific binding of magnetic particles to cells is, in part, a function of the interaction between positively charged sites on magnetic particles and negatively charged sialic acid residues on cell surfaces. Therefore, by adding negatively charged substances to positively charged magnetic particles, a blocking of these positive sites occurs, imparting greater negative surface charge to the particles and, thereby reducing the non-specific binding to cells. As proof of this phenomenon, eight positively charged materials (2 proteins, 6 polymers), when tested separately in the buffer used to dilute colloidal magnetic particles, had extremely adverse effects, significantly increasing the non-specific binding of particles to cells.

To eight tubes (numbered 9-16) 150 ul of $CR^{51}$ labelled human T-cells (cells same as in Example 1 but at $3.26 \times 10^6$ cells/ml) was added. Tube 9 contained the cells combined with 150 ul of buffer A (described in Example 1) supplemented with 5% (w/v) BSA. Tube 10 contained 150 ul of colloid 08314-1 diluted to 0.02 mg/ml iron in buffer A supplemented with 5% BSA. Each of the remaining tubes contained 150 ul colloid as above, diluted as above in buffer A supplemented with 5% BSA and varying amounts of Tamol 850, from 0.125% to 4% (w/v), the amount of Tamol 850 doubling in each successive tube. In all cases, the colloid was diluted in the appropriate buffer and allowed to stand 30 minutes at room temperature for blocking to occur prior to use. Also, all percentages of Tamol 850 used were based on active material. The final reaction mixtures containing cells and colloids were incubated 15 minutes at room temperature during which time they were counted in a gamma counter for $CR^{51}$ to determine the total number of cells per mixture, vortexed, and incubated another 15 minutes at 4° C.

Then, an aliquot (250 ul) of test medium from each tube was transferred to a separate microtiter well assigned the same identifying number. As in Example 1, the material remaining in each tube, after removal of the 250 ul aliquot, was counted in a gamma counter. Next, a pair of wire loops was inserted into each microtiter well and the insertion into the magnet, the separation and the analysis were performed as in Example 1; however, no wash step was used.

The results obtained are set forth in Table 2.

TABLE 2

| Sample No. | No. of Cells in Test Medium | No. of Cells Separated On Wire Loops | Percentage of Cells Separated (No Wash) |
|---|---|---|---|
| 9 | 410487 | 4807 | 1.17 |
| 10 | 403651 | 326004 | 80.76 |
| 11 | 411055 | 32313 | 7.86 |
| 12 | 425781 | 36126 | 8.48 |
| 13 | 432738 | 30304 | 7.00 |
| 14 | 406633 | 27384 | 6.73 |
| 15 | 427870 | 42251 | 9.87 |
| 16 | 426552 | 138073 | 32.37 |

Referring to Table 2, a high reduction of the non-specific binding of colloidal magnetic particles to human T-cells was achieved when using Tamol 850 within a range of approximately 0.1% to 2%. Other anionic polyelectrolytes found to work similarly to Tamol 850 include Heparin (anticoagulant used to collect blood), Daxad 30 (an anionic surfactant similar to Tamol 850 - made by W.R. Grace & Co., Lexington, Mass.), Polywet ND-2 (an anionic dispersant made by Uniroyal Chemical, Middlebury, Conn.), Aerosol OS (an anionic surfactant made by American Cyanamid Co., Wayne, N.J.) and D-glucuronic acid (Sigma No. G-8645), all of which carry a net negative charge at the neutral pH range.

EXAMPLE 3

The magnetic separator described in Example 1 was tested to determine if coating the wire loops changed the effectiveness of the apparatus in separating cells and/or colloidal magnetic particles from the test medium and to determine the effectiveness of these coatings for recovering separated cells by removal from the wire loops after the separation step.

In each of 6 test tubes (numbered 17-22), 150 ul of $CR^{51}$-labelled human T-cells identified in Example 1 ($2.46 \times 10^6$ cells/mL) were mixed with 150 ul of the above-described Colloid No. 08314-1 and 20 ul phosphate buffered saline ("PBS"). In each of another six tubes (numbered 23-28), 150 ul of $CR^{51}$-labelled human T-cells, as above, was combined with 150 ul of Colloid No. 08314-1 and 20 ul CD45 Mab (described in Example 1) and incubated for 15 minutes at room temperature along with tubes 17-22 during which time the tubes were counted in a gamma counter to determine the total cpm, thereby determining the total number of cells, as was done in Example 1. For tubes 17-28, Colloid No. 08314-1 was first diluted to 0.02 mg/mL iron as was done in Example 1, except that in the present example, buffer A was supplemented with 1% Tamol 850 (w/v) and 5% BSA (w/v). Furthermore, in tubes 23-28, the diluted colloid was preincubated with the CD45 Mab for 1 hour at room temperature prior to combining with cells.

Then, an aliquot (250 ul) of each test medium was transferred from each of tubes 17-28 to a separate, serially connected set of microtiter wells, which were assigned the same identifying number. As in Example 1, the material remaining in tubes 17-28 after removing the 250 ul was counted in a gamma counter. Into each microtiter well was inserted a pair of magnetic metal loops. The pairs of loops inserted into wells 17, 18, 23 and 24 were uncoated. The pairs of loops inserted into wells 19, 20, 25 and 26 had been coated previously with three coats of a clear acrylic enamel coating. The pairs of loops inserted into wells 21, 22 and 27, 28 had been coated previously with three coats of a white acrylic coating (appliance gloss white). Both the clear acrylic coating and the white acrylic coating are available from Yenkin-Majestic Paint Corp., Colombus, Ohio under the trademark "MAJIC Spray".

The wells with loops inserted therein were placed between the two magnets used in Example 1. The test media in wells 17-28 were exposed to a magnetic field for 5 minutes at room temperature, after which the wells (now containing the supernatant) were removed from the field, separated and counted in a gamma counter to assess the counts from $CR^{51}$ and thereby cells remaining in these supernatants. As in Example 1, the cells immobilized on the wire loops which were still in the magnetic field were washed and these supernatants were counted for $CR^{51}$ in a gamma counter. Next, the wire loops from tests 17-28 were removed from the magnetic field and inserted into new microtiter wells (also labelled 17-28) which contained 250 ul of buffer A with 1% BSA (w/v). The plastic frame housing the wire loops was then simply raised and lowered several times during a 1 minute period after which time the microtiter wells were separted and inserted into counting tubes and then into a gamma counter to determine the number of cells removed from the wire loops using this process.

TABLE 3

| Sample No. | Surface of loops | No. of cells in test medium | No. of cells separated on wire loops (no wash) | Percentage of cells separated on wire loops (no wash) | Percentage of cells separated on wire loops (one wash) | Percentage of cells recovered from the wire loops |
| --- | --- | --- | --- | --- | --- | --- |
| 17 | Uncoated | 280,054 | 17,097 | 6.10 | 5.10 | N.C. |
| 18 | do | 278,427 | 21,798 | 7.83 | 6.88 | N.C. |
| 19 | Clear Acrylic | 275,547 | 13,083 | 4.75 | 3.79 | N.C. |
| 20 | do | 275,477 | 13,455 | 4.88 | 4.18 | N.C. |
| 21 | White Acrylic | 276,466 | 13,158 | 4.76 | 3.85 | N.C. |
| 22 | do | 277,384 | 8,591 | 3.10 | 2.48 | N.C. |
| 23 | Uncoated | 257,761 | 200,253 | 77.69 | 76.45 | 20.50 |
| 24 | do | 246,827 | 192,083 | 77.82 | 76.55 | 21.26 |
| 25 | Clear Acrylic | 256,932 | 201,512 | 78.43 | 76.95 | 38.31 |
| 26 | do | 248,842 | 193,666 | 77.83 | 75.97 | 41.9 |
| 27 | White Acrylic | 251,598 | 194,103 | 77.15 | 75.35 | 36.05 |
| 28 | do | 242,120 | 189,414 | 78.26 | 77.04 | 34.47 |

N.C. indicates that the cells were not counted.

The results obtained from this experiment are reported in Table 3. Referring to Table 3, the cells retained on the coated wire loops were transferred to the buffer solution in far higher percentages than cells attached to the uncoated loops. Thus, coating of the wire loops tends to ease removal of the cell-bearing magnetic particles from the loops.

EXAMPLE 4

The magnetic separator described in Example 1 above was used to separate colloidal magnetic particles and a target substance which in this case was human T-cells being separated from both peripheral blood mononuclear cells and whole blood, thereby showing the effectiveness of this separator and process for separating cells from complex matrices. In this example, the CD4 antigen (T-helper cell antigen) on the T-cell was targeted with the colloidal particle.

A colloidal magnetic particle was prepared similarly to those described in Example 1 except that the concentration of affinity purified goat anti-mouse Fc antibody was 700 ug/mL. The resultant colloid was 1 mg/mL iron. This colloid (Colloid No. 07075-1) was then diluted to 0.2 mg/mL iron in a buffer. The buffer was buffer A supplemented with 5% BSA (w/v) and 1% Tamol 850 (w/v on an active basis) final pH 7.25. This composition will herein be referred to as buffer B. The colloid was allowed to stand at least 30 minutes before use.

Whole blood was drawn into Becton Dickenson EDTA ($K_3$) liquid vacutainers and peripheral blood mononuclear cells (PBMC's) were isolated using Histopaque 1077 (Sigma Diagnostics, Sigma procedure no. 1077). The PBMCs were washed 3 times in isotonic PBS, pH 7.2, and resuspended in a balanced salt solution (BSS), pH 7.2, containing 1% BSA (w/v). Red blood cells, from above, were washed 3 times in isotonic PBS and recombined with the previously separated plasma component. Human T-cells (as per Example 1 which were known to also express the CD4 antigen) were $CR^{51}$ labelled and spiked in one case (1) into the above described pBMCs and, in a second case (2) into a mixture of PBMCs and the above plasma/red blood cell mixture. In both cases (wells 29–44), the $CR^{51}$ labelled T-cells were used at a concentration to yield approximately 200,000 T-cells per test or 200,000 T-cells per 117.65 ul which is the volume all cells occupied in the 250 ul reaction volume. In case 1 above (wells 29–36), the 117.65 ul contained approximately 400,000 PBMCs and in case 2 (wells 37–44), the 117.65 ul contained 400,000 PBMCs and $2.9 \times 10^8$ red blood cells.

Wells 29, 30, 37 and 38 contained 117.65 ul. buffer B, 14.7 ul. PBS and 117.65 ul of case 1 cells, as above, for wells 29 and 30, and case 2 cells, as above, for wells 37 and 38. Wells 31, 32, 39 and 40 contained 117.65 of the above colloid, 14.7 ul PBS and 117.65 ul of case 1 cells, as above, for wells 31 and 32 and case 2 cells, as above, for wells 39 and 40. Wells 33, 34, 41 and 42 contained 117.65 ul of the above colloid, 14.7 ul of anti-CD4 Mab (obtained from Gen Trak, Inc., Plymouth Meeting, Pa., purified $IgG_1$ form in PBS at 100 ug/mL) and 117.65 ul of case 1 cells above for wells 33 and 34 and case 2 cells above for wells 41 and 42. Wells 35, 36, 43 and 44 contained 117.65 ul of the above colloid, 14.7 ul of 100 ug/mL non-specific $IgG_1$ Mab (Sigma MOPC21, Sigma No. M-7894 diluted to 100 ug/mL in PBS, 0.1% BSA) and 117.65 ul of case 1 cells above for wells 35 and 36 and case 2 cells above for wells 43 and 44.

In all cases, the Mab was preincubated with the cells for 5 minutes at room temperature, followed by a minute incubation with colloid and a 3 minute separation. All reaction mixtures were made up in 12 ×75 mm glass tubes at approximately 1.3 times the volumes shown above in order to perform the quantitation as per examples 1, 2 and 3, where the actual reaction volume per test was 250 ul. The reaction mixtures were transferred from the 12×75 mm tubes to a serially connected set of microtiter wells assigned the same identifying numbers indicated above. Furthermore, the total cpm was obtained when only cells were present in the reaction tubes prior to adding the other reagents due to the short incubation times. In this experiment, the magnetic configuration shown in FIG. 1 was equipped with a plastic elevation system which facilitated the raising and lowering of the microtiter wells into and out of the magnetic field (raised up into the field such that there was 1 pair of wire loops in each microtiter well as in Examples 1, 2 and 3, and then down and out of the field after the separation time, so that the wire loops remained in the field and the supernatants in each well were removed). The HGMS time in this example was 3 minutes.

The results of the just described experiment are shown in Table 4:

TABLE 4

| Well No. | Cells * Present | cpm in 250 ul | cpm in Supernatant | Percentage of T-cells Separated |
|---|---|---|---|---|
| 29 | T + P | 69946 | 67200 | 3.92 |
| 30 | " | 77494 | 74938 | 3.30 |
| 31 | " | 84697 | 79553 | 6.07 |
| 32 | " | 78351 | 73700 | 5.94 |
| 33 | " | 66574 | 12223 | 81.64 |
| 34 | " | 61921 | 11177 | 81.95 |
| 35 | " | 61728 | 57926 | 6.16 |
| 36 | " | 69309 | 64814 | 6.49 |
| 37 | T + P + R | 43115 | 41341 | 4.11 |
| 38 | " | 44094 | 42151 | 4.41 |
| 39 | " | 67678 | 63107 | 6.75 |
| 40 | " | 57945 | 54431 | 6.06 |
| 41 | " | 58774 | 10530 | 82.08 |
| 42 | " | 74447 | 12337 | 83.43 |
| 43 | " | 49578 | 46057 | 7.10 |
| 44 | " | 77761 | 73066 | 6.04 |

* T = T-cells, P = PMBCs, R = Red Cells

The data shown in Table 4 show the high percentage of T-cells (specifically T-helper cells) that were separated from these complex mixture using the magnetic separator and separation process described herein. The differences in the percentages of T-cells separated from wells 29 and 30 versus 31 and 32 and for wells 37 and 38 versus 39 and 40, indicate that approximately 60–70% of the T-cells removed in these tests were removed without colloidal particles being present. This has been identified as the removal of free CR[51] which is in the liquid remaining on the wire loops after lowering the microtiter wells out of the field. Therefore, the percent non-specific binding of colloidal particles to cells is actually even lower than the numbers seen for wells 31, 32, 39 and 40.

It is also noteworthy that no increase (compared to the controls) in the number of T-cells separated was seen when substituting a non-specific Mab for the specific anti-CD4 Mab (wells 35, 36, 43 and 44).

EXAMPLE 5

Effect of 'Layering' Colloid Upon HGMS and Quantitation in Immunoassays

When colloidal magnetic materials are deposited on a surface (e.g., a magnetic gradient intensifying member) in a uniform or an almost uniform monolayer, immunochemical analysis can be performed in a novel manner. For example, in the single wire-in-capillary or triangular grid devices (Examples 6–9) following receptor/ligand reaction and after the bound/free separation is performed in these devices, certain analytical steps such as washing, enzyme/substrate reaction or further immunochemical reaction can be done directly on the magnetically immobilized material without the need to resuspend the magnetic material. This novel approach considerably simplifies such analyses. It is made possible by the very significant increase in surface area obtained with the colloidal sized particles, as well as the concomitant decrease in the mass of separation media required; hence, the analyses described herein can be performed in a manner totally different from those employing large particulate materials. To illustrate the operation of this principle, the following observations, theoretical calculations and experimental data are given.

For magnetic immobilization on the single wire device when quantities of a colloid are employed such that a visible coating forms, magnetic material is observed on the sides of the wire facing the pole pieces, i.e. transverse to the field as predicted by HGMS theory. For the triangular grid device, the same coating pattern is observed, except significantly more material layers onto the region of the grids corresponding to the outer surfaces of double-thick wire, i.e. where two wires cross or intersect. For the grids, these outer surfaces or "spots" where collection predominates always face the pole pieces and, like the single wire, are transverse to the field. When lesser amounts of colloidal material are employed with the grids, microscopic examination shows that immobilization takes place for the most part only on the outer surfaces corresponding to the regions where two wires cross and not on other surfaces of the grids. Further, the "spots" where collection takes place are twice as long (along the wire axis) as they are wide. Hence, an estimate of that surface area can be calculated. To construct triangular grids, 1.5×1.0 cm. strips of screen were used, composed of 16 pieces of wire 1.5 cm long and 25 pieces 1.0 cm. long. The number of intersections from such a grid is 400 (25×16) and as collection takes place on the front and back of the intersections transverse to the field there are 800 such collection "spots". For these and if a "spot" is approximated as a rectangle of 0.025 cm.×0.050 cm. then the collection area where the first monolayer will form is 800×0.025 cm.×0.050 cm which equals 1 cm$^2$.

Table 5 shows results of an experiment employing the triangular grid devices in concert with an avidin colloid of 80 nm. diameter. The magnetic colloid used in this example was prepared similarly to those described in Example 1, above, with the concentration of avidin in the resulting colloid being 150 ug/ml. For this experiment, 2 monoclonals to human Chorionic Gonadotrophic (hCG) were used (Medix, Foster City, Calif.). Further, the capture monoclonal was biotinylated and the labelling MAB coupled to alkaline phosphatase. To determine the importance of developing what is effectively a monolayer of the colloid in these novel protocols, the "0" and 100 m IU/mL hCG standard were first incubated with fixed quantities of capture and labelling Mab and sufficient avidin colloid (determined to be 7.5 ug Fe) to capture all of the formed sandwiches. Quantitation of enzyme captured in the "0" and 100 m IU/mL standard was performed by washing the magnetically immobilized colloid followed by determination of enzyme activity directly on the magnetically immobilized material. Absorbance was measured at 405 nm. As described previously, all of these operations were done in the magnetic field, i.e. without resuspension of the magnetic material. Next, analyses were performed using the same quantities of Mab's but with increased quantities of the avidin colloid. As all the sandwiches were captured with the lowest level of colloid used (7.5 ug), layering upon separation or magnetic immobilization will occur when the surface capacity of the collector is exceeded. The results of such experiments are set forth in Table 5, as well as the surface areas required to "monolayer" the different amounts of colloid employed in each experiment. The latter were obtained by assuming that the monolayer is "square" packed such that each colloid occupies an area approximately 85×85 nm on a side (taking into account the target substance borne by the 80 nm colloid). Further, the correspondence of colloid and iron for this avidin sample is $1.8 \times 10^9$ colloid particles per ug. of iron. From Table 5, it is seen that the "0" standard is lowest for the 7.5 ug Fe experiment and more than doubles for the 45 ug Fe colloid experiment. In the case of the 100 m IU/mL standard, the 7.5 ug Fe colloid value is 1.75 and decreases substantially when the amount of colloid employed doubles and dramatically at the highest level employed. From the column showing the surface area required to "monolayer" the various amounts of colloid employed, it is apparent that the lowest level employed which clearly gives the best signal has a value of 0.98 cm². That value very closely approximates to the estimated 'first monolayer' collection area of the triangular grids employed.

TABLE 5

Effect of 'layering' Colloid upon HGMS and Signal Output

| ug Fe | Monolayer* Surface Area (cm²) | hCG Standards [Abs$_{405}$] | |
|---|---|---|---|
| | | "0" Std. | 100 mIu Std. |
| 7.5 | 0.98 | 0.068 | 1.75 |
| 15.0 | 1.95 | 0.068 | 1.50 |
| 30 | 3.90 | 0.109 | 1.29 |
| 45 | 5.80 | 0.153 | 1.18 |

* Calculated in accordance with the preceding description.

Since the amount of sandwiches captured by the avidin should be the same in all cases (7.5 ug Fe is a capacity well in excess of that required to capture all of the biotinylated antibody based on experimental as well as theoretical considerations), the decrease in enzyme activity using higher levels of the capture colloid are consistent with layering which inhibits the substrate access to 'buried' enzyme. Similarly, the rise in the "0" standard value with increasing amounts of colloid indicates that layering traps enzyme labelled MAB which otherwise is washed away in the "monolayer" experimental condition. This result further suggests that the diminution of signal seen in the 100 mIU/mL standard experiments has a high bias since trapped enzyme-MAB would contribute to the values obtained at the highest level of the colloid used. Thus, that result likely would be worse were it not for trapped material. As material so trapped is a random event, high coefficients of variation are likely to result unless conditions are employed which give rise to the development of a substantial monolayer of the magnetic colloid.

For experiments done with the wire-in-capillary device, as illustrated in FIG. 8, 10 cm. lengths of 0.025 cm. diameter single wires have been employed for immobilization of the colloid. Such a wire has 0.82 cm² of surface area, approximately half of which (0.41 cm²) serves to immobilize the colloid in the transverse field configuration. For 80 nm particles "square" packed, as above, 4 ug of Fe would create a monolayer. For 50-60 nm particles coated with antibody and packed in "squares" 65×65 nm, 1.4 ug of Fe would create a monolayer. When colloids in this size range were used to perform sandwich assays in this configuration and by the non-resuspension methodology described, low end level and high end effects became apparent when more than 2 ug of Fe was used.

EXAMPLE 6

Separations were performed using a magnetic separator having the configuration shown in FIG. 5, provided with a triangular shaped magnetic metal screen (grid) open at both ends, with the apexes in functional contact with the inner walls of each microtiter well. Some of the triangular screens employed were painted or lacquered to determine the effect of such a coating on the performance of an estradiol immunoassay.

Quadruplets of the 'zero' standard were assayed using non-coated, painted and lacquered metal screens. A comparison was also made to determine the effect of carrying out the substrate incubation inside or outside the magnetic field using the painted grids. Standards were prepared in human serum (Scantibodies Lab., Santee, Calif.) containing from 0–3000 pg/mL of estradiol. Typical reaction mixtures were prepared by mixing 200 ul of 'zero' standard, 50 ul alkaline phosphatase conjugated estradiol at a suitable dilution and 50 ul of a colloid containing goat anti-mouse (Fc) antibodies (Jackson Immuno-research Lab., Westgrove, Pa.) to which was immuno-specifically attached a monoclonal anti-estradiol antibody. The magnetic colloid used in this example was prepared similarly to those described in Example 1, above, with the concentrations of GAMFc and iron being 0.5 mg/ml and 0.9 mg/ml, respectively. The monoclonal was used at a final dilution of 1/10,000 in this colloid reagent. The mixtures were incubated for 15 minutes at 37° C. in test tubes and then transferred to a serially connected set of 8 grid-in-microtiter wells positioned between two magnets that created a 6.5 kGauss external magnetic field. Then, high gradient magnetic separation was allowed to take place for 3 minutes, during which time all the colloidal magnetite particles became magnetically attracted towards and adhered to the wire screens. Next, a wash step was carried out by inversion of the magnet containing the grids-in-wells so as to decant the contents from the wells followed by blotting of the wells gently against several layers of absorbant paper. Next, with the grids-in-wells still disposed in the magnetic field, each well was filled with wash buffer, then decanted and blotted dry as explained above. This wash process was repeated once more. Then, 300 ul of enzyme substrate (20 mM p-nitrophenylphosphate; Sigma Chemical Company, St. Louis, Mo.) was added to each grid-in-well still disposed in the magnetic field and allowed to incubate for 15 minutes at 37°. Then, 50 ul of stop solution (7M NaOH) was added to each grid-in-well while still in the magnetic field and the contents of each well mixed with the aid of a multi-channel pipettor. The color intensity of the resultant enzymatic product in each grid-in-well was measured along the central vertical axis of the well (the triangular region formed by the grid) using an Immunoplate reader (NJ-2000, Inter-Lab., Newbury Park, Calif.) at 405 nm. This operation was done after removal of the set of 8 grid-in-wells from the magnet and placing them in a suitable microtiter plate frame. During the time interval required to make this measurement the colloid remained on the grids. Apparently, there is sufficient residual field on the grids to retain the colloid.

The results of these experiments are shown in Table 6. As can be seen from Table 6, the use of painted or lacquered screens resulted in higher signals, i.e. higher levels of binding, as compared with the unpainted screens. Also, the coefficients of variation for the coated screens may be as low as about 1%, indicating that the coatings assist in minimizing experimental error and in obtaining greater reproducibility of results.

TABLE 6

| | MEAN | STANDARD DEVIATION | COEFFICIENT OF VARIATION |
|---|---|---|---|
| UNPAINTED | 1.315 | 0.053 | 4.1% |
| PAINTED | 2.095 | 0.050 | 2.4% |
| UNPAINTED | 1.426 | 0.090 | 6.3% |
| LACQUERED | 1.944 | 0.023 | 1.2% |
| SUBSTRATE INC. INSIDE FIELD | 1.717 | 0.051 | 3.0% |
| SUBSTRATE INC. OUTSIDE FIELD | 2.108 | 0.053 | 2.5% |

EXAMPLE 7

An 'hCG' (human chorionic gonadotrophin) sandwich-type immunoassay was performed using the magnetic separator and vessel as depicted in FIG. 5 with the triangular shaped magnetic metal screens contained in microtiter wells. Standards were prepared in human serum containing 0, 5, 25, 50, 100 and 500 mIU/ml 'hCG' (Sigma Chemical Co., St. Louis, Mo.). Typical reaction mixtures were prepared by mixing 200 ul standard, 50 ul of a mixture containing biotin-labelled capture monoclonal and alkaline-phosphatase labelled monoclonal (Medix Biotech, Inc., Foster City, Calif.) and 5 ul of an avidin coated colloid prepared as described in Example 5, above. The reaction mixtures were incubated for 30 minutes at room temperature and then transferred into a serially connected set of 8 grid-in-microtiter wells positioned between two magnets that created a 6.5 kGauss magnetic field. All subsequent steps in this assay were carried out exactly as described in Example 6 except that the substrate incubation was performed at room temperature. Determinations were done in duplicate for each standard and the results noted in Table 7.

TABLE 7

| STANDARD (mIU/ml) | 0 | 5 | 25 | 50 | 100 | 500 |
|---|---|---|---|---|---|---|
| ABSORBANCE (at 405 nm) | 0.045 | 0.178 | 0.534 | 0.910 | 1.654 | 3.124 |

EXAMPLE 8

The magnetic separtor described in Example 6 was used to develop a dose-response curve for an estradiol enzyme-immunoassay over a clinically significant range using painted triangular shaped screens as the magnetic field gradient intensifier. As in Example 6, estradiol standards of varying concentrations (0–4000 pg/mL) were used. Typical reaction mixtures were prepared by mixing 200 ul of standard, 50 ul of alkaline phosphatase conjugated estradiol and 50 ul of a goat anti-mouse (Fc) colloid to which was immunospecifically coupled a monoclonal anti-estradiol antibody. The colloid was prepared as described in Example 6, above. The monoclonal was used at a final dilution of 1/10,000 in this colloid reagent. The reaction mixtures were incubated for 15 minutes at 37° C. in test tubes and then transferred into a serially connected set of 8 grid-in-microtiter wells positioned between two magnets that created a 6.5 KGauss magnetic field. All subsequent steps in this assay were carried out exactly as described in Example 6. Determinations were carried out in duplicate for each standard and the results obtained are set forth in Table 8.

TABLE 8

| Estradiol Standard pg./ml. | 0 | 30 | 50 | 100 | 300 | 1000 | 4000 |
|---|---|---|---|---|---|---|---|
| Absorbance (405 nm) | 1.895 | 1.734 | 1.683 | 1.609 | 1.423 | 0.967 | 0.36 |

For the "0" standard, a coefficient of variation of 1.6% was determined for 10 replicates, with a standard deviation of +/− 0.030.

EXAMPLE 9

Another embodiment of the magnetic separation apparatus of the invention, utilizing a series of eight 100 ul. capacity capillary tubes, each containing a single 4" strand of 0.01" diameter magnetic wire, as shown in FIG. 8, was employed in performing a sandwich-type immunoassay.

In this example, mouse immunoglobulin (IgG) (Jackson Immunoresearch Labs., Westgrove, Pa.) was used as the analyte. Standards containing mouse IgG at various levels (0–4000 ng/mL) were prepared in 5% BSA, phosphate buffered saline and 0.1% sodium azide. Typical rection mixtures were prepared by mixing 60 ul of standard, 20 ul of goat anti-mouse (Fab) - alkaline phosphatase conjugate (Sigma Chemical Company, St. Louis, Mo.) and 20 ul of a colloid containing affinity purified goat anti-mouse (Fc) antibodies. The colloid was prepared as described in Example 1, above. The reaction mixtures were incubated for 30 minutes at room temperature and then pumped into the capillary tubes with the aid of a syringe infusion pump (Harvard Apparatus, South Natick, Mass.) The capillary tubes were then placed into a 8 KGauss magnetic field and magnetic separation was performed for 2 minutes. During this period, all the colloid magnetite particles became magnetically attracted and adhered to the wire surface. The capillary tubes were then washed by flowing 390 ul of buffer through them. Then, 130 ul of enzyme substrate (20 mM p-nitrophenyl-phosphate) was pumped into the capillaries. After a 5 minute incubation within the magnetic field, the enzymatic product was pumped out into the microtiter wells containing stop solution (6M $H_2SO_4$) and the absorbance at 405 nm was recorded using an Immunoplate reader. As was the case with the triangular grid-in-well examples, the above-mentioned steps in this assay, i.e. washing of the immobilized colloid on the wire, substrate addition and substrate incubation were performed with the capillary tubes disposed in the magnetic field (i.e. without resuspending the magnetic material).

Determinations were carried out in duplicate for each standard and the results obtained are set forth in Table 9.

TABLE 9

| Mouse IgG (ng/ml) | 0 | 62.5 | 125 | 250 | 500 | 1000 | 2000 | 4000 |
|---|---|---|---|---|---|---|---|---|

TABLE 9-continued

| Absorbance 405 nm. | 0.026 | 0.160 | 0.195 | 0.295 | 0.483 | 0.570 | 0.806 | 0.837 |
|---|---|---|---|---|---|---|---|---|

As can be seen from the data in Table 9, the increase in concentration of target substance in the test medium produces corresponding increases in the absorbance readings.

While various aspects of the present invention have been described and exemplified above in terms of certain preferred embodiments, various other embodiments may be apparent to those skilled in the art. The invention is, therefore, not limited to the embodiments specifically described and exemplified, but is capable of variation and modification without departing from the spirit of the invention, the full scope of which is delineated by the appended claims.

What is claimed is:

1. A magnetic separator used to separate magnetic particles from a non-magnetic test medium in which said magnetic particles are suspended, the separator comprising:
   a) a non-magnetic container having an opening for receiving said test medium and defining a separation chamber;
   b) one or more magnetic wires, each having a longitudinal axis, positioned within the container and effective in said test medium to intensify a magnetic field gradient generated in the test medium by an applied magnetic field, said one or more wires each being in the form of a loop having spaced apart ends so that the surfaces of said wires do not form capillaries, pockets, or interstices which might entrap non-magnetic components of the test medium, and a carried connected to said ends of said wires disposed outside of said separation chamber; and
   c) magnetic means having poles confronting each other for generating magnetic flux lines extending between the poles transverse to the longitudinal axis of said wires to generate a magnetic field gradient operative upon the magnetic particles within the test medium to attract said magnetic particles toward the magnetized wires and cause such particles to be adhered to the wires.

2. A magnetic separator as claimed in claim 1, wherein said magnetic wires are disposed within said container with sufficient rigidity to resist substantial deformation when passed into or out of a magnetic field of 4-15 kGauss.

3. A magnetic separator as claimed in claim 1, wherein said one or more magnetic wires have a diameter of between about 0.8 mm and about 3.0 mm.

4. A magnetic separator as claimed in claim 1, wherein said wires are coated with a coating material capable of facilitating the removal of said particles from the surface of said wires.

5. A magnetic separator as claimed in claim 1, wherein said wire is in the shape of two substantially parallel semicircular loops having respective ends attached to said carrier.

6. A magnetic separator as claimed in claim 5, wherein said magnetic means comprise confronting magnets and the carrier is non-magnetic and is adapted to be mounted upon the confronting magnets.

7. A magnetic separator as claimed in claim 6, wherein said confronting magnets generate a field of about 7.0 to about 8.5 kGauss.

8. A magnetic separator as claimed in claim 1, wherein the separator also comprises a particle collector used to collect the magnetic particles remaining adhered to the magnetized wire after the container holding the test medium is removed from the wire, said particles being adapted to be separated from the wire and transferred to said particle collector.

9. A magnetic separator used to separate magnetic particles from a non-magnetic test medium in which said magnetic particles are suspended, the separator comprising:
   a) a non-magnetic container having an opening for receiving said test medium and defining a separation chamber;
   b) one or more magnetic wires, each having a longitudinal axis, positioned within the container and effective in said test medium to intensify a magnetic field gradient generated in the test medium by an applied magnetic field, and a carrier for said wires disposed outside of said separation chamber; and
   c) magnetic means having pole pieces confronting each other for generating magnetic flux lines extending between the pole pieces transverse to the longitudinal axis of said wires to generate a magnetic field gradient operative upon the magnetic particles within the test medium to attract said magnetic particles toward the magnetized wires and cause such particles to be adhered to the wires, wherein said non-magnetic container comprises a microtiter well.

10. A magnetic separator used to separate magnetic particles from a non-magnetic test medium in which said magnetic particles are suspended, the separator comprising:
    a) a non-magnetic container having an opening for receiving said test medium and defining a separation chamber;
    b) one or more magnetic wires, each having a longitudinal axis, positioned within the container and effective in said test medium to intensify a magnetic field gradient generated in the test medium by an applied magnetic field, and a carrier for said wires disposed outside of said separation chamber; and
    c) magnetic means having pole pieces confronting each other for generating magnetic flux lines extending between the pole pieces transverse to the longitudinal axis of said wires to generate a magnetic field gradient operative upon the magnetic particles within the test medium to attract said magnetic particles toward the magnetized wires and cause such particles to be adhered to the wires, wherein said non-magnetic container comprises a capillary tube.

11. A magnetic separator used to separate magnetic particles from a non-magnetic test medium in which said particles are suspended, the separator comprising:
    a) a non-magnetic container with an open top capable of receiving the test medium;
    b) a wire screen both adapted to be held in a fixed position within the container and formed into a triangularly shaped body having a central cavity and open at both ends; and c) magnetic means for applying a magnetic field substantially transverse to the longitudinal axis of the wires in said wire screen to generate a magnetic field gradient operative upon the magnetic particles within the test medium to attract said magnetic particles toward the magnetized screen and cause such particles to be adhered to the screen.

12. A magnetic separator as claimed in claim 11, wherein the container also comprises a particle collector used to collect the magnetic particles remaining adhered to the magnetized screen after the test medium is decanted from the container holding the screen, said particles being adapted to be separated from the screen and collected in said particle collector.

13. A magnetic separator as claimed in claim 12, wherein the screen is coated with a coating material capable of facilitating the removal of the particles from the surface of the screen.

14. A magnetic separator as claimed in claim 11, wherein the magnetic means for applying the magnetic field comprises confronting magnets positioned on opposite sides of the non-magnetic container holding the wire screen.

15. A magnetic separator as claimed in claim 14, wherein said confronting magnets generate a field of about 7.0 to about 8.5 kGauss.

16. A magnetic separator used to separate magnetic particles from a non-magnetic test medium in which said magnetic particles are suspended, the separator comprising:

a) an array of capillary tubes, each of said tubes having an opening for receiving said test medium;

b) one or more magnetic wires disposed within the capillary tubes and substantially in contact with said test medium;

c) magnetic means for applying a magnetic field substantially transverse to the longitudinal axis of said wires to generate a magnetic field gradient operative upon the magnetic particles within the test medium to attract said magnetic particles toward the magnetized wires and cause such particles to be adhered to the wires.

17. A magnetic separator used to separate magnetic particles from a non-magnetic test medium in which said magnetic particles are suspended, the separator comprising:

a) an array of interconnected non-magnetic microtiter wells, each with an open top capable of receiving said test medium;

b) one or more magnetic wires capable of being disposed substantially within each of the microtiter wells and in contact with said test medium;

c) magnetic means for applying a magnetic field transverse to the longitudinal axis of said wires to generate a magnetic field gradient operative upon the magnetic particles within the test medium to attract said magnetic particles toward the magnetized wires and cause such particles to be adhered to the wires.

18. A magnetic separator as claimed in claim 17 wherein said wires are in the form of semicircular loops having end portions, and including a holder engaging said end portions and positioning said loops in said wells.

19. A magnetic separator as claimed in claim 17 wherein said wires comprise a wire screen formed into a hollow shape open at both ends and held in a fixed position within the container.

20. A magnetic separator as claimed in claim 19 wherein said wire screen comprises a triangularly shaped body.

21. A method for magnetically separating a target substance from a non-magnetic test medium in a magnetic separator comprising a container with an open top, magnetic wire means positioned within the container providing an exposed surface area and magnetic means for magnetizing the magnetic wire means, the method comprising the steps of:

a) contacting a quantity of magnetic particles comprising a receptor capable of binding specifically to said target substance within said test medium under conditions causing binding of said receptor to said target substance, resulting in target substance-bearing magnetic particles;

b) introducing said test medium in which said magnetic particles are suspended into said container holding said magnetic wire means; and c) positioning said container holding magnetic wire means and said test medium having the suspension of magnetic particles therein adjacent to said magnetic means in order to generate in said test medium a magnetic field gradient operative upon the magnetic particles within the test medium to attract said magnetic particles to the exposed surface area of the magnetized wire and cause such particles to be adhered to said exposed surface, and d) controlling the quantity of magnetic particles introduced into the container relative to the exposed surface area of said wire means, and controlling the orientation of said exposed surface area causing said particles to adhere to the surface area in a substantially single layer corresponding in thickness to about the size of said target-substance bearing magnetic particles.

22. A method as claimed in claim 21 including the step of maintaining the magnetic particles adhered to the magnetic wire means within said container while removing the non-magnetic test medium from the container.

23. A method as claimed in claim 22 including the step of washing the magnetic particles adhered to the magnetic wire means to remove residual test medium from the magnetic particles and from the magnetic wire means.

24. A method as claimed in claim 23 including the step of removing from the container the magnetic wire means with the magnetic particles adhered thereto, immersing the magnetic wire means into a resuspension medium and subjecting said magnetic wire means to conditions causing resuspension of said magnetic particles in said resuspension medium.

25. A method for determining a target substance in a test medium suspected of containing said target substance, said method comprising:

a) contacting said test medium with a quantity of colloidal magnetic particles comprising or adapted to comprise a receptor capable of binding specifically to said target substance, under conditions causing binding of said target substance to said receptor, resulting in target substance-bearing magnetic particles;

b) introducing said test medium into a separation chamber containing a magnetic field gradient intensifier comprising filamentary material having a magnetic field applied thereto, whereby said magnetic particles are caused to adhere to said filamentary material;

c) removing said test medium from said separation chamber;

d) treating said magnetic particles while adhered to said filamentary material for removal of interfering substances; and e) determining the target substance by analysis of said magnetic particles or said removed test medium.

26. A method according to claim 25 wherein said filamentary material comprises at least one ferromagnetic wire which is disposed within said separation chamber with sufficient rigidity to resist substantial deformation when passed into or out of a magnetic field of 4–15 KGauss.

27. A method according to claim 26, wherein said wire has a diameter from about 0.8 mm. to about 3 mm.

28. A method according to claim 25, wherein said quantity of magnetic particles is controlled, relative to the exposed surface area of said filamentary material and the orientation of said exposed surface is controlled, so as to cause said magnetic particles to adhere to said exposed surface in a substantially single layer corresponding in thickness to about the size of said target-substance bearing magnetic particles.

29. A method according to claim 25, wherein said magnetic particles comprise a transition metal oxide substantially surrounded by a biofunctional polymer having available coordination sites, in proportions rendering said magnetic particles resuspendable.

30. A method according to claim 29, wherein said transition metal oxide is magnetite and said biofunctional polymer is a protein or a polymer capable of being coupled to a protein.

31. A method according to claim 25, which is performed without resuspension of said magnetic particles.

32. A method according to claim 25, which is performed batchwise.

33. A method according to claim 25, wherein said test medium comprises a detectable label whose occurrence in association with said magnetic particles, or in said removed test medium is detected in determining said target substance.

34. A method according to claim 33, wherein said test medium comprises an enzyme-linked receptor for said target substance.

35. A method according to claim 34, wherein said determination of said target substance comprises detecting the activity of said enzyme by contacting with a chromogenic substance producing a detectable color, and detecting the appearance or relative intensity of said color by reference to a standard.

36. A method according to claim 35, wherein detecting the activity of said enzyme is performed with said magnetic particles adhered to said filamentary material.

37. A method for determining an immunoreactive ligand in a test sample suspected of containing said ligand, said method comprising:

a) contacting said test sample with a quantity of colloidal magnetic particles comprising or adapted to comprise a first receptor to said ligand, and a second, enzyme-linked receptor to said ligand, under conditions causing binding of said receptors to said ligand, resulting in enzyme and target-substance bearing magnetic particles.

b) introducing said test medium into a separation chamber including at least one ferromagnetic wire disposed in said chamber with sufficient rigidity to resist substantial deformation when passed into or out of a magnetic field of 4–15 K Gauss and having a magnetic field applied thereto, thereby to produce a magnetic field gradient operative upon said magnetic particles, causing said particles to adhere to said wire;

c) washing said magnetic particles to remove unbound substances; and d) determining the activity of said enzyme bound to said particles, as a measure of the presence or quantity of said ligand in said test sample.

38. A method as claimed in claim 37, wherein said ligand is an antigen and said first and second receptors are antibodies capable of specific interaction with said antigen.

39. A method as claimed in claim 38, wherein said antigen is a cell-surface antigen.

40. A method according to claim 37, wherein said determination of ligand comprises contacting said enzyme with a chromogenic substance producing a detectable color and detecting the appearance or relative intensity of said color by reference to a standard.

41. A method according to claim 40, wherein detecting the activity of said enzyme is performed with said magnetic particles adhered to said filamentary material.

42. A method according to claim 37, wherein said quantity of magnetic particles is controlled, relative to the exposed surface area of said filamentary material, and the orientation of said exposed surface is controlled, so as to cause said magnetic particles to adhere to said surface in a substantially single layer corresponding in thickness to about the size of said enzyme and target-substance bearing magnetic particles.

* * * * *

UNITED STATES PATENT AND TRADEMARK OFFICE
CERTIFICATE OF CORRECTION

PATENT NO. : 5,200,084
DATED : April 6, 1993
INVENTOR(S) : Paul A. Liberti; Brian P. Feeley; Dhanesh I. Gohel It is certified that error appears in the above-identified patent and that said Letters Patent is hereby corrected as shown below:

Column 18, line 50, after "by a" insert --2--;

Column 19, line 28, "mixture" should be --mixtures--;

Column 20, line 29, after "For these" insert --experiments, wire 0.025 cm. in diameter was employed--.

Signed and Sealed this

Thirtieth Day of November, 1993

Attest:

BRUCE LEHMAN

*Attesting Officer*   *Commissioner of Patents and Trademarks*